United States Patent
Vallapureddy et al.

(10) Patent No.: US 7,218,969 B2
(45) Date of Patent: May 15, 2007

(54) DYNAMIC CHANNEL SELECTION FOR RF TELEMETRY WITH IMPLANTABLE DEVICE

(75) Inventors: Vineel Vallapureddy, St. Paul, MN (US); Cynthia Morrissey, St. Paul, MN (US); Paul Holmquist, Andover, MN (US); Earle Roberts, Maple Grove, MN (US); Joseph E. Bange, Eagan, MN (US); Jeffrey A. Von Arx, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 72 days.

(21) Appl. No.: 11/039,200

(22) Filed: Jan. 19, 2005

(65) Prior Publication Data

US 2006/0161223 A1  Jul. 20, 2006

(51) Int. Cl.
*A61N 1/00* (2006.01)
(52) U.S. Cl. ............................ 607/60; 607/30; 607/31; 607/32; 128/901; 128/903
(58) Field of Classification Search ............ 607/30–32, 607/60; 128/901, 903
See application file for complete search history.

(56) References Cited

U.S. PATENT DOCUMENTS

| | | | |
|---|---|---|---|
| 4,404,972 A | 9/1983 | Gordon et al. | |
| 4,441,498 A | 4/1984 | Nordling | |
| 4,519,401 A | 5/1985 | Ko et al. | |
| 4,562,841 A | 1/1986 | Brockway et al. | |
| 5,342,408 A | * 8/1994 | deCoriolis et al. ............ 607/32 |
| 5,562,713 A | 10/1996 | Silvian | |
| 5,683,432 A | 11/1997 | Goedeke et al. | |
| 5,694,952 A | 12/1997 | Lidman et al. | |
| 5,725,559 A | 3/1998 | Alt et al. | |
| 5,843,139 A | 12/1998 | Goedeke et al. | |
| 5,861,019 A | 1/1999 | Sun et al. | |
| 6,044,485 A | 3/2000 | Dent et al. | |
| 6,169,925 B1 | 1/2001 | Villaseca et al. | |
| 6,385,318 B1 | 5/2002 | Oishi | |
| 6,424,867 B1 | 7/2002 | Snell et al. | |
| 6,427,088 B1 | 7/2002 | Bowman, IV et al. | |

(Continued)

FOREIGN PATENT DOCUMENTS

WO    WO-2005099817 A1    10/2005

(Continued)

OTHER PUBLICATIONS

Bange, Joseph E., et al., "Implantable Medical Device Telemetry with Adaptive Frequency Hopping", U.S. Appl. No. 11/456,937, filed Jul. 12, 2006, 35 pages.

(Continued)

*Primary Examiner*—Robert E. Pezzuto
*Assistant Examiner*—Natasha Patel
(74) *Attorney, Agent, or Firm*—Schwegman, Lundberg, Woessner, & Kluth, P.A.

(57) ABSTRACT

A telemetry system for radio-frequency communications between an implantable medical device and an external device providing improved noise immunity is disclosed. Multiple communications channels are used to enable establishment and re-establishment of communications between a particular pair of devices in a multiple device environment.

20 Claims, 3 Drawing Sheets

U.S. PATENT DOCUMENTS

| | | |
|---|---|---|
| 6,434,429 B1 | 8/2002 | Kraus et al. |
| 6,443,891 B1 | 9/2002 | Grevious |
| 6,463,329 B1 | 10/2002 | Goedeke |
| 6,470,215 B1 | 10/2002 | Kraus et al. |
| 6,482,154 B1 | 11/2002 | Haubrich et al. |
| 6,535,766 B1 | 3/2003 | Thompson et al. |
| 6,564,104 B2 | 5/2003 | Nelson et al. |
| 6,564,105 B2 | 5/2003 | Starkweather et al. |
| 6,574,510 B2 | 6/2003 | Von Arx et al. |
| 6,585,644 B2 | 7/2003 | Lebel et al. |
| 6,600,952 B1 | 7/2003 | Snell et al. |
| 6,602,191 B2 | 8/2003 | Quy |
| 6,622,050 B2 | 9/2003 | Thompson |
| 6,687,546 B2 | 2/2004 | Lebel et al. |
| 6,763,269 B2 | 7/2004 | Cox |
| 6,801,807 B2 * | 10/2004 | Abrahamson ............... 607/60 |
| 6,868,288 B2 * | 3/2005 | Thompson .................. 607/31 |
| 6,985,773 B2 | 1/2006 | Von Arx et al. |
| 7,013,178 B2 * | 3/2006 | Reinke et al. ............... 607/60 |
| 2002/0115912 A1 | 8/2002 | Muraki et al. |
| 2002/0143372 A1 | 10/2002 | Snell et al. |
| 2002/0147388 A1 | 10/2002 | Mass et al. |
| 2003/0083719 A1 | 5/2003 | Shankar et al. |
| 2003/0114897 A1 | 6/2003 | Von Arx et al. |
| 2003/0114898 A1 | 6/2003 | Von Arx et al. |
| 2003/0146835 A1 | 8/2003 | Carter |
| 2004/0030260 A1 | 2/2004 | Von Arx |
| 2004/0260363 A1 | 12/2004 | Arx et al. |
| 2005/0204134 A1 | 9/2005 | Von Arx et al. |
| 2005/0240245 A1 | 10/2005 | Bange et al. |
| 2005/0283208 A1 | 12/2005 | Von Arx et al. |
| 2006/0025834 A1 | 2/2006 | Von Arx et al. |
| 2006/0030901 A1 | 2/2006 | Quiles et al. |
| 2006/0030902 A1 | 2/2006 | Quiles et al. |
| 2006/0030903 A1 * | 2/2006 | Seeberger et al. ............ 607/60 |
| 2006/0030904 A1 | 2/2006 | Quiles |

FOREIGN PATENT DOCUMENTS

| | | |
|---|---|---|
| WO | WO-2006020546 A1 | 2/2006 |
| WO | WO-2006020549 A1 | 2/2006 |

OTHER PUBLICATIONS

Bange, Joseph E., et al., "Implantable Medical Device Telemetry with Periodic Frequency Hopping", U.S. Appl. No. 11/456,942, filed Jul. 12, 2006, 43 Pages.

Healy, S. J., et al., "System and Method for Providing Secure Exchange of Sensitive Information with an Implantable Medical Device", U.S. Appl. No. 10/801,150, filed Mar. 15, 2004, 30 pgs.

* cited by examiner

DYNAMIC CHANNEL SELECTION FOR RF TELEMETRY WITH IMPLANTABLE DEVICE

FIELD OF THE INVENTION

This invention pertains to implantable medical devices such as cardiac pacemakers and implantable cardioverter/defibrillators. In particular, the invention relates to a system and method for implementing telemetry in such devices.

BACKGROUND

Implantable medical devices (IMDs), including cardiac rhythm management devices such as pacemakers and implantable cardioverter/defibrillators, typically have the capability to communicate data with an external device (ED) via a radio-frequency telemetry link. One such external device is an external programmer used to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations.

External programmers are commonly configured to communicate with an IMD over an inductive link. Coil antennas in the external programmer and the IMD are inductively coupled so that data can be transmitted by modulating a carrier waveform which corresponds to the resonant frequency of the two coupled coils. An inductive link is a short-range communications channel requiring that the coil antenna of the external device be in close proximity to the IMD, typically within a few inches. Other types of telemetry systems may utilize far-field radio-frequency (RF) electromagnetic radiation to enable communications between an IMD and an ED over a wireless medium. Such long-range RF telemetry allows the IMD to communicate with an ED, such as an external programmer or remote monitor, without the need for close proximity. In either the home or the clinic, however, there are external sources of RF energy which may interfere with communication between the ED and IMD.

It is also common in clinical settings for there to be multiple implantable and/or external devices are present in an area so that communication over the wireless medium is possible between the multiple devices. Access to the medium among the multiple devices must be controlled in this situation in order for a communications session between any pair of devices to be established. It would also be desirable for there to be the possibility of multiple communications sessions between different devices occurring concurrently.

SUMMARY

The present disclosure relates to an RF telemetry system and method for enabling communication between an implantable medical device and an external device with an improved tolerance to noise from external sources. Multiple communications channels at different frequencies are provided which may be dynamically switched between during a communications session. In one embodiment, both devices are programmed to switch to different channels according to a predetermined scheme during the communications session. In another embodiment, the devices switch to a different channel when the quality of the presently used channel has degraded to an unacceptable level.

DETAILED DESCRIPTION

Described below is a system and method for providing wireless RF telemetry between an implantable medical device and an external device with improved tolerance to external noise. Most noise from external sources is of the narrow-band type, where the energy of the noise is confined to a particular frequency range. Examples of narrow-band noise sources include communications devices such as wireless telephones as well as many other kinds of electronic equipment which are commonly found in the home and in the clinic. When such narrow-band noise is in the same frequency range used for telemetry, it is said to be in-band and can interfere with communications between the devices. In order to deal with the problem of in-band noise, the available bandwidth of the wireless medium is divided into multiple communications channels at different frequencies. At any given time, only the channels at the same frequency as the in-band noise are interfered with. In one embodiment, the external device and implantable device are programmed to switch from channel to channel at predetermined times according to a switching algorithm during a communications session in order to minimize the effects of noise in one of the channels.

In another embodiment, after a communications session is established and data transfer is taking place on one of the channels, the external device is programmed to monitor the quality of the channel so that a switch to another channel can be made if the channel currently being used has become degraded due to external noise. Channel quality may be monitored, for example, by monitoring particular quality parameter, such as the data transfer rate or throughput, during a communications session and comparing it to a threshold value. Alternative quality parameters such as the error rate, the number of repeated frames during a communications session, or the length of time in which no data transfer has taken place could also be compared to threshold values. If one or more quality parameters indicate that the channel quality has degraded to an unacceptable level and is thus effectively disabled, the external device may then be programmed to find an available unused channel with an acceptable noise level and switch the communications session with the implantable device to new channel. The channel switching may be accomplished by the external device communicating the new channel information to the implantable device, either over the presently used but degraded channel or over a predetermined alternate channel, and both devices then switching to the new channel. In the case where an alternate channel is to be used to communicate the new channel information, both the external and implantable device may be programmed to revert to a designated alternate channel if no communications are received over the currently used channel for a specified period of time. Multiple alternate channels may be provided for this purpose to allow for the possibility that an alternate channel may also be so degraded by noise that no communications are possible, with alternate channels being used in a defined sequence. It is also possible for an alternate channel which is reverted to by both devices to be used as the new channel for continuing the communications process. The channel switching process as just described may be repeated as necessary during the communications session.

The multiple channels provided for noise reduction may also be used to allow concurrent communications between multiple devices over the common wireless medium. This is especially desirable in a clinical environment where there may be a number of external and implantable devices in range of one another. In one embodiment, a number of the channels are designated as data channels, each of which can be used for data transfer between an external and an implantable device, and one or more of the other channels are designated as control channels over which the devices communicate in order to establish a communications session by transmitting control frames. Once a communications session is established between two devices, one of the devices finds and selects an unused data channel and commands the other device over the control channel to utilize the selected data channel for further communications during which data transfer takes place. A control channel may also be used as a designated alternate channel so that both devices switch back to a specified control channel if the selected data channel becomes disabled. The data channel selection process is then repeated, and the devices switch to the selected data channel to continue the communications session.

As described above, dynamic channel selection for providing improved noise immunity may be employed in a number of different wireless communications regimes. Various alternative embodiments are described in detail below after a description of exemplary hardware components.

1. Exemplary Hardware Platform

Figure 1:
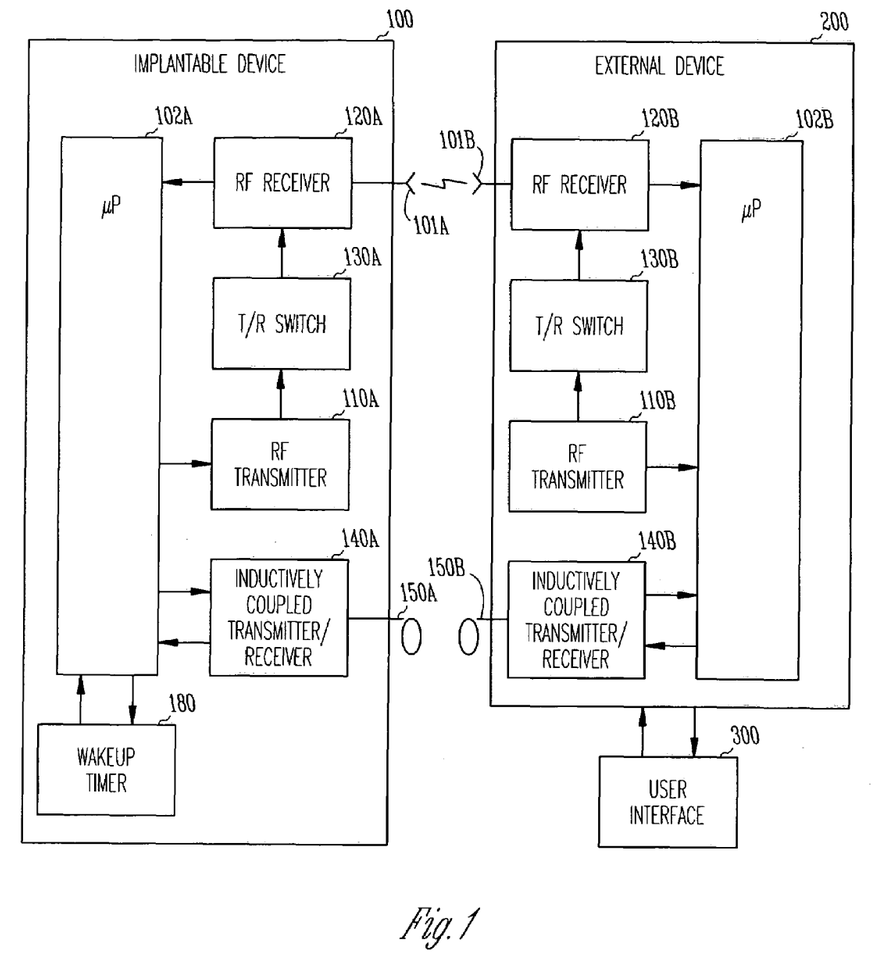
FIG. 1 is a block diagram of a telemetry system for an implantable device and an external device.

FIG. 1 shows the primary telemetry components of an external device 200 and an implantable medical device 100. In this functional block diagram, the components are shown as being identical in each device. In this exemplary embodiment, the external device and the implantable device are microprocessor-based devices each having a controller 102a or 102b that includes a microprocessor and memory for data and program storage that supervises overall device operation as well as telemetry. Code executed by the controller also implements the dynamic channel selection schemes to be described below. The implantable device 100 may be a cardiac rhythm management device such as a pacemaker or implantable cardioverter/defibrillator, while the external device 200 may be an external programmer or a data-gathering device such as remote monitor. A user interface 300 (e.g., a keyboard and monitor) may be provided to enable a user such as a clinician to direct the operation of the external device.

A long-range RF receiver 120a or 120b and a long-range RF transmitter 110a or 110b are interfaced to the microprocessor 102a or 102b in the implantable device and the external device, respectively. Also in each device, the transmitter and receiver are coupled to an antenna 101a or 101b through a transmit/receive switch 130a or 130b. The transmit/receive switches 130a and 130b are controlled by the microprocessor and either passes radio-frequency signals from the transmitter to the antenna or from the antenna to the receiver to establish an RF link. To effect communications between the devices over the RF link, a radio-frequency carrier signal modulated with digital data is transmitted wirelessly from one antenna to the other. A demodulator for extracting digital data from the carrier signal is incorporated into each receiver, and a modulator for modulating the carrier signal with digital data is incorporated into each transmitter. The interface to the controller for the RF transmitter and receiver in each device enables data transfer. The RF receiver and transmitter of each device are tunable and may be switched among a plurality of communications channels which differ in frequency. The implantable device also incorporates a means by which the controller can power up or power down the RF receiver and/or transmitter in order to manage duty cycles. A wakeup timer 180 for defining the RF duty cycle is also shown for the implantable device, and this timer can either be implemented in code executed by the controller or can be discrete components. FIG. 1 also shows an inductively coupled transmitter/receiver 140a or 140b and antenna 150a or 150b for the implantable and external devices by which communication may take place over an inductive link when the two devices are in close physical proximity to one another.

2. Exemplary Channel Selection Schemes

In the embodiments described below, the controllers of the external and implantable devices are programmed to operate their respective telemetry hardware in a manner which utilizes multiple communications channels. The multiple channels are defined with different carrier frequencies so that communications over one channel does not disturb communications over any of the other channels. A dynamic channel selection scheme is then employed to avoid channels which are corrupted with external noise. Two example embodiments are described, each of which utilizes multiple data channels for transmitting data between an external device and an implantable device. In the first embodiment, the data channels are also used to transmit control information for initiating a communications session. In the second embodiment one or more channels are designated as control channels and dedicated to the transmission of control information.

Figure 2:
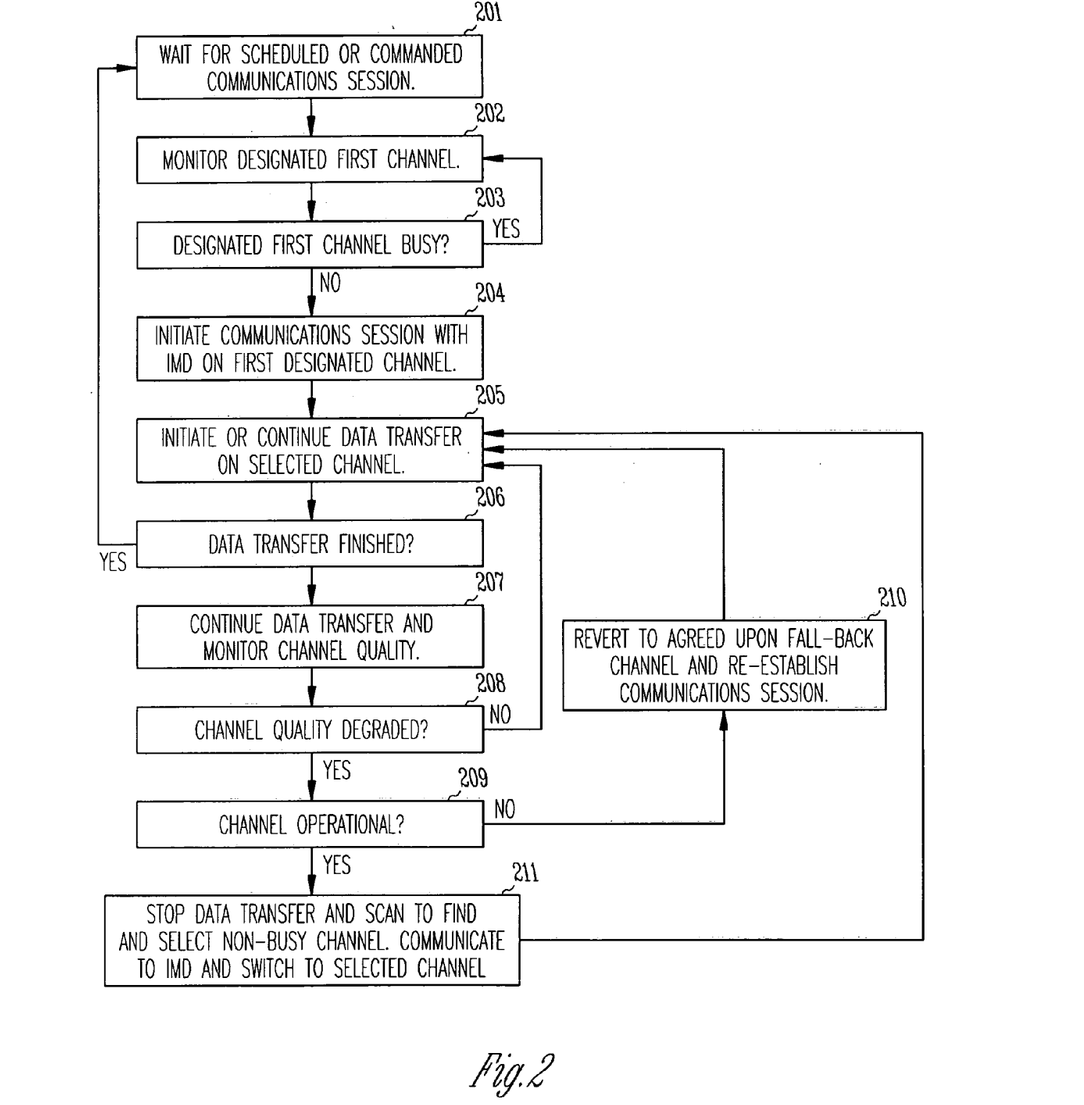
FIG. 2 illustrates an exemplary embodiment of a scheme for dynamic channel selection.

FIG. 2 illustrates the steps performed by the external device controller in communicating with an implantable device via a long-range RF telemetry link according to one embodiment. In this embodiment, multiple channels are provided with each channel capable of being used for both initiating communications sessions and transferring data. At step 201, the external device waits until a communications session with an implantable device is scheduled to occur by a programmed command or until a command is received via a user interface to initiate a communications session. After either type of command, the external device monitors a designated first channel for activity at step 202. The designated first channel is a particular one of the multiple channels which both devices have agreed to use first for establishing a communications session. The choice of a designated first channel may be communicated from the external device to the implantable device using the inductive link or during a previous communications session using long-range telemetry. The device continues to monitor the designated first channel until the channel is found to be not busy at step 203. Then, at step 204, a communications session is initiated, and data transfer begins at step 205. When the data transfer has been completed, as determined at step 206, the device returns to step 201. As the data is being transferred, the external device monitors the channel quality at step 207 and continues transferring data on the selected channel if no channel degradation is detected at step 208. If channel degradation is detected to the extent that the channel is non-operational, as determined at step 209, the external device and the implantable device both revert to a previously agreed upon fall-back channel at step 210 where the communications session is re-established by transmission of control frames. If the fall-back channel is not available, either because of interference or because it is busy, a plurality of previously agreed upon fall-back channels may be reverted to in a specified sequence. A timeout duration may be specified for each fall-back channel so that if no communications are established within the timeout duration, the devices move to the next fall-back channel in the sequence. Data transfer then continues at step 205 either on the fall-back channel or on a channel selected by the external device and communicated to the implantable device via the fall-back channel. If, at step 209, it is determined that the channel is degraded to an unacceptable level but is still operational, the external device ceases transferring data and begins scanning to find another non-busy channel at step 211. Such scanning may be performed over all of the multiple channels or over a specified and agreed upon sub-group or pool of channels. After selection of another channel, the external device communicates the information to the implantable device over the presently used channel. Both devices then switch to the selected channel and continue to transfer data at step 205.

Figure 3:
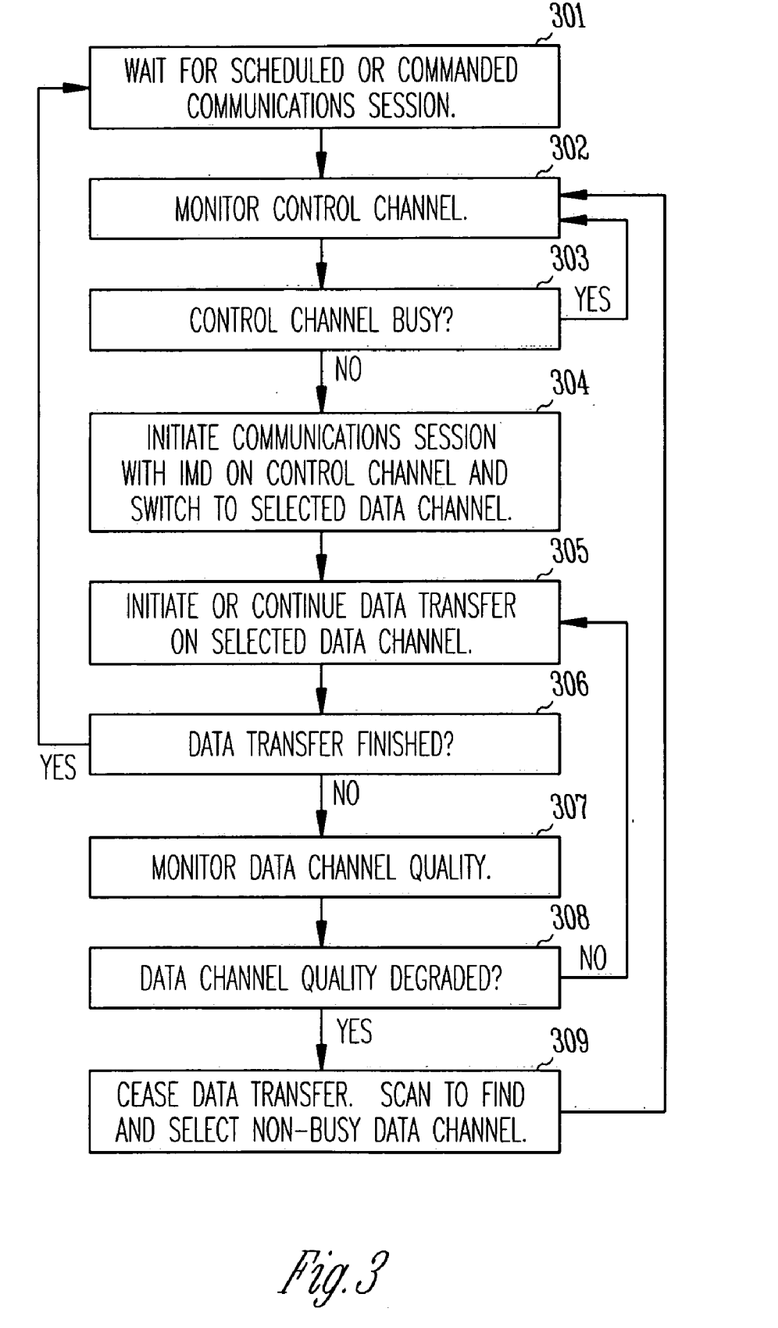
FIG. 3 illustrates an exemplary embodiment of a scheme for dynamic channel selection which employs separate data and control channels.

In another embodiment, the multiple channels are divided into data channels and one or more control channels, the former used for data transfer and the latter used for transmitting control frames in order to initiate and maintain a communications session. When multiple devices are in range of one another and want to access the common wireless medium, the embodiment as described with reference to FIG. 2 may cause delays in initiating a communications session between a pair of devices if the designated first channel is presently being used for data transfer by another pair of devices. By dedicating a control channel to the transmission of control frames only, it becomes more likely that a pair of devices will be able to access the control channel without delay and initiate a communications session. FIG. 3 illustrates a dynamic channel selection scheme which utilizes a single control channel for use by multiple devices in initiating communications sessions. (Other embodiments may employ a plurality of such control channels.) At step 301, the external device waits for a scheduled or manually input command to initiate a communications session. After such a command, the control channel is monitored for activity at step 302 until it becomes available. When the control channel is not busy, as determined at step 303, a communications session is initiated with a selected implantable device via the transmission of control frames over the control channel at step 304. Also transmitted to the implantable device over the control channel as part of a control frame is the identification of a data channel selected by the external device for use in the subsequent data transfer. Both devices then switch to the selected data channel for further transfer of data. When the data transfer has been completed, as determined at step 306, the device returns to step 301. As the data is being transferred, the external device monitors the channel quality of the data channel at step 307 and continues transferring data on the selected data channel if no channel degradation is detected at step 308. If channel degradation is detected, either to the extent that the data channel is non-operational or merely unacceptable, the external device ceases transferring data and begins scanning to find another non-busy channel at step 309. The scanning may cover all data channels or a specified sub-group of the data channels. After selection of another data channel, the external device returns to step 302 to wait for access to the control channel. A communications session is then re-established with the implantable device at step 304, and an identification of the selected data channel is transmitted to the implantable device. Both devices then switch to the selected data channel and continue to transfer data at step 305.

Various techniques may be used in implementing the functions performed by the embodiments described above. Examples of such techniques are described in the following paragraphs.

Initiation of a communications session may involve a handshaking procedure in which control frames are transmitted to synchronize the subsequent activity of both devices. For example, when the external device wishes to transmit data, an RTS frame is transmitted to the implantable device which then responds with a CTS frame. Similarly, when the external device wishes to receive data, an RRTS frame is transmitted to the implantable device, the implantable device responds with an RTS frame, and the external device transmits a CTS frame. One or more of the control frames may also contain other information such as the device ID, amount of data to be transmitted, and an identification of which channel is to be used for data transfer. The device receiving a CTS frame then begins transmitting data frames. During the data transfer, data frames sent by one of the devices are acknowledged by the other device with an ACK frame and repeated if necessary in order to ensure reliable data transmission.

At various points in the embodiments described above, the external device searches for an available data channel by checking the data channels for activity. One way the external device may do this is to tune its receiver to a particular data channel and listen for a valid preamble known to be transmitted by all devices during the transmission of data frames. If no such preambles are detected over a specified time period (e.g., 200 msec) in a particular data channel, the external device can assume that the data channel is not being used. Alternatively, the external device may tune to a particular data channel and measure its signal strength over a specified period of time. If the peak signal strength over some period of time (e.g., 200 msec) is less than some defined value (e.g., −75 dBm where −85 dBm is considered the noise floor), then the data channel can be assumed to be clear and available for use. In another alternative, preamble detection and signal strength measurement can be combined so that a data channel is assumed to be available for use only if no preambles are detected and the peak signal strength is below a certain value over some period of time. However the availability of channels is determined, if a data channel is determined to be busy, the external device can proceed to check the other data channels for activity either randomly or in a defined sequence.

Once a communications session has been established and data transfer is taking place over a selected data channel, environmental noise or other factors may disrupt communications over the channel. Both the external and implantable devices may be programmed to monitor the data transfer in order to determine if the quality of the link has fallen below a specified level so as to constitute an interruption of the communications session. For example, a communications interruption may be declared if the channel throughput falls below a certain level over a certain time (e.g., below 50% of channel capacity for 1 second), if a specified number of data frames are unacknowledged, and/or if the frame error rate exceeds a threshold value. Upon declaration of an interrupted session, both devices may be programmed to revert back to either a selected data channel or a control channel. After a clear and available data channel is found, the communications session is re-initiated, and the devices switch to the new data channel for data transfer.

Control channels are also subject to interference from environmental noise or may suffer from degradation due to other factors. To deal with this problem, multiple control channels may be provided. For example, two control channels may be utilized with one designated as the primary control channel and the other designated as the secondary control channel. In an example embodiment, the primary control channel is always used for both connect and reconnect communications unless it is unavailable due to excess noise or other factors, in which case the secondary control channel is used. Excess noise in a control channel may be determined, for example, if the average signal strength exceeds a threshold value over a specified period of time (greater than −75 dBm over at least a 500 msec period) with no valid preambles being detected. In another embodiment, two connect control channels and two reconnect control channels are provided. The implantable device in an interrupted session first listens on the reconnect channel which is most isolated from the data channel that failed (e.g., farthest away in frequency). After some period of time (e.g., 500 msec), the implantable device begins cycling between the two reconnect channels, listening for some period of time on one channel (e.g., 200 msec) before switching to the other channel. In a similar fashion, the external device in an interrupted session also moves to the reconnect channel which is most isolated from the failed data channel and begins transmitting control frames (i.e., RRTS or RTS). If no response is received from the implantable device after some period of time (e.g., 500 msec), the external device cycles between the two reconnect control channels, transmitting control frames for some period of time (e.g., 50 msec) on each channel before moving to the other channel.

As described earlier with reference to FIG. 1, the implantable device may be equipped with a wake up timer for the telemetry components in order to conserve energy. An implantable device not engaged in an active communications session must wake up periodically in order to monitor transmissions on the control channel or designated first data channel and determine if an external device is attempting to communicate with it. In an embodiment utilizing primary and secondary control channels, the implantable device may wake up to check for a signal on both the primary and secondary control channels, alternate between the control channels during each wakeup, or check for a signal on the primary control channel more frequently than it wakes up to check for a signal on the secondary control channel. For example, an implantable device not in an active communications session may wake up every 10 seconds to check the primary channel and wake up every 1 minute to check the secondary channel. The external device may transmit control frames alternately over each control channel at shorter intervals (e.g., 50 msec).

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A telemetry system for enabling radio-frequency (RF) communications between an implantable medical device and an external device over a wireless medium, comprising:
   an antenna, an RF transmitter, an RF receiver, and a controller incorporated into each of the implantable and external devices,
   wherein the RF transmitter and receiver of each device are tunable and may be switched among a plurality of different communications channels which differ in frequency;
   wherein the controller is interfaced to the RF transmitter and receiver in each device to enable establishment of a communications session and data transfer over a selected channel;
   wherein the external device and implantable device controllers are programmed to establish a communications session over one of a plurality of designated control channels;
   after establishment of a communications session, the external device controller is programmed to search among a plurality of designated data channels to select an unused data channel and transmit an identification of the selected channel to the implantable device;
   wherein the external device and implantable device controllers are programmed to switch to the selected data channel for subsequent data transfer during the communications session;
   wherein the external device and implantable device controllers are programmed to revert to the designated control channel that is farthest away in frequency from the selected data channel upon a degradation in the quality of the selected data channel sufficient to constitute a failure in the selected data channel.

2. The system of claim 1 wherein the external device controller is programmed to monitor the quality of a communications channel by determining if the channel throughput over a certain time falls below a certain level.

3. The system of claim 1 wherein the external device controller is programmed to monitor the quality of a communications channel by determining if a specified number of data frames are unacknowledged.

4. The system of claim 1 wherein the external device controller is programmed to monitor the quality of a communications channel by determining if the frame error rate exceeds a threshold value.

5. The system of claim 1 wherein the implantable device and external device controllers are programmed to cycle among designated control channels after a specified period time if the devices are unable to establish communications over the designated control channel farthest away in frequency from the selected data channel that failed.

6. The system of claim 1 wherein the external device and implantable device controllers are programmed to attempt to re-establish communications over another designated data channel after reverting to one of the designated control channels upon a failure in the selected data channel.

7. The system of claim 6 wherein the external device controller is programmed to search for an available data channel by checking the data channels for activity.

8. The system of claim 7 wherein the external device controller is programmed to tune its receiver to a particular data channel, listen for a valid preamble known to be transmitted by all devices during the transmission of data frames, and regard the data channel as unused if no such preambles are detected over a specified time period.

9. The system of claim 7 wherein the external device controller is programmed to tune its receiver to a particular data channel, measure the signal strength of the channel over a specified period of time, and regard the channel as unused if the peak signal strength over specified period of time is less than a specified value.

10. The system of claim 7 wherein the external device controller is programmed to:
   tune its receiver to a particular data channel;
   listen for a valid preamble known to be transmitted by all devices during the transmission of data frames;
   measure the signal strength of the channel over a specified period of time; and,
   regard the data channel as unused if no such preambles are detected over a specified time period and if the peak signal strength over specified period of time is less than a specified value.

11. A method by which an implantable medical device and an external device may communicate over a wireless medium, comprising:
   providing a plurality of different communications channels which differ in frequency;
   programming the external device and implantable device to establish a communications session over one of a plurality of designated control channels;
   programming the external device controller to search among a plurality of designated data channels to select an unused data channel and transmit an identification of the selected channel to the implantable device after establishment of a communications session over a designated control channel;
   programming the external device and implantable device to switch to the selected data channel for subsequent data transfer during the communications session; and,
   programming the external device and implantable device to revert to the designated control channel that is farthest away in frequency from the selected data channel upon a degradation in the Quality of the selected data channel sufficient to constitute a failure in the selected data channel.

12. The method of claim 11 further comprising programming the external device to monitor the quality of a communications channel by determining if the channel throughput over a certain time falls below a certain level.

13. The method of claim 11 further comprising programming the external device to monitor the quality of a communications channel by determining if a specified number of data frames are unacknowledged.

14. The method of claim 11 further comprising programming the external device to monitor the quality of a communications channel by determining if the frame error rate exceeds a threshold value.

15. The method of claim 11 further comprising programming the implantable and external devices to cycle among designated control channels after a specified period time if the devices are unable to establish communications over the designated control channel farthest away in frequency from the selected data channel that failed.

16. The method of claim 11 further comprising programming the external and implantable devices to attempt to re-establish communications over another designated data channel after reverting to one of the designated control channels upon a failure in the selected data channel.

17. The method of claim 16 further comprising programming the external device to searching for an available data channel by checking the data channels for activity.

18. The method of claim 17 further comprising programming the external device to listen to a particular data channel for a valid preamble known to be transmitted by all devices during the transmission of data frames and regard the data channel as unused if no such preambles are detected over a specified time period.

19. The method of claim 17 further comprising programming the external device to measure the signal strength of a particular data channel over a specified period of time and regard the channel as unused if the peak signal strength over specified period of time is less than a specified value.

20. The method of claim 17 further comprising programming the external device to:
   listening to a particular data channel for a valid preamble known to be transmitted by all devices during the transmission of data frames;
   measuring the signal strength of the particular data channel over a specified period of time; and,
   regarding the data channel as unused if no such preambles are detected over a specified time period and if the peak signal strength over specified period of time is less than a specified value.

* * * * *

UNITED STATES PATENT AND TRADEMARK OFFICE
CERTIFICATE OF CORRECTION

PATENT NO. : 7,218,969 B2
APPLICATION NO. : 11/039200
DATED : May 15, 2007
INVENTOR(S) : Vallapureddy et al.

It is certified that error appears in the above-identified patent and that said Letters Patent is hereby corrected as shown below:

In column 9, line 38, in Claim 11, delete "Quality" and insert -- quality --, therefor.

In column 10, line 20 (Approx.), in Claim 17, delete "searching" and insert -- search --, therefor.

In column 10, lines 22-23 (Approx.), in Claim 18, delete "programing" and insert -- programming --, therefor.

In column 10, lines 33-34, in Claim 20, delete "programing" and insert -- programming --, therefor.

Signed and Sealed this

Twenty-fourth Day of July, 2007

JON W. DUDAS
*Director of the United States Patent and Trademark Office*